(12) United States Patent
Orbay et al.

(10) Patent No.: US 11,129,725 B2
(45) Date of Patent: Sep. 28, 2021

(54) DISTAL RADIOULNAR JOINT PROSTHESIS SYSTEM AND METHOD OF USE

(71) Applicants: Jorge L. Orbay, Miami, FL (US); Edward J. Tremols, Miami, FL (US); Brian A. Cooke, Miami, FL (US)

(72) Inventors: Jorge L. Orbay, Miami, FL (US); Edward J. Tremols, Miami, FL (US); Brian A. Cooke, Miami, FL (US)

(73) Assignee: Skeletal Dynamics, Inc., Miami, FL (US)

( * ) Notice: Subject to any disclaimer, the term of this patent is extended or adjusted under 35 U.S.C. 154(b) by 0 days.

(21) Appl. No.: 16/909,726

(22) Filed: Jun. 23, 2020

(65) Prior Publication Data

US 2020/0397591 A1    Dec. 24, 2020

Related U.S. Application Data

(60) Provisional application No. 62/865,442, filed on Jun. 24, 2019.

(51) Int. Cl.
*A61F 2/42*     (2006.01)
*A61F 2/30*     (2006.01)
*A61F 2/46*     (2006.01)

(52) U.S. Cl.
CPC .......... *A61F 2/4261* (2013.01); *A61F 2/4606* (2013.01); *A61F 2002/3021* (2013.01); *A61F 2002/30507* (2013.01); *A61F 2002/4269* (2013.01)

(58) Field of Classification Search
CPC ...... A61B 17/86; A61F 2/4606; A61F 2/4261; A61F 2002/30507
See application file for complete search history.

(56) References Cited

U.S. PATENT DOCUMENTS

| | | | |
|---|---|---|---|
| 6,302,915 B1 | 10/2001 | Cooney, III et al. | |
| 7,819,924 B2 | 10/2010 | Vander Meulen et al. | |
| 8,512,412 B2 | 8/2013 | Hanson et al. | |
| 9,549,826 B2 | 1/2017 | Cooney, III et al. | |

(Continued)

FOREIGN PATENT DOCUMENTS

WO    WO2018077421    5/2018

OTHER PUBLICATIONS

International Application No. PCT/US20/39183—Patent Cooperation Treaty PCT International Search Report—Completed Sep. 22, 2020 (dated Oct. 13, 2020).

(Continued)

*Primary Examiner* — Marcia L Watkins
(74) *Attorney, Agent, or Firm* — Lott & Fischer, P.L.

(57) ABSTRACT

Disclosed is a distal radio ulnar joint prosthesis system, and the method of use for the same, the system comprising an ulnar stem component, and ulnar head component, a set screw, and a sigmoid notch component, the system providing a prosthesis for replacement of the distal radio ulnar joint to restore the pronation-supination motion of the forearm as well as stability between the ulna and radius; a DRUJ prosthesis adapted for rotational alignment of the replacement joint along the axis of forearm rotation; a DRUJ prosthesis which allows for the use of a number of different sized heads having differing geometries; a DRUJ prosthesis adapted for variable pivoting alignment between the replacement distal ulnar head and the ulna; and a DRUJ prosthesis adapted for adjustment in the alignment between the articulating surface of the ulnar head and the sigmoid notch.

7 Claims, 10 Drawing Sheets

(56) References Cited

U.S. PATENT DOCUMENTS

| | | |
|---|---|---|
| 2006/0142866 A1 | 6/2006 | Baratz et al. |
| 2009/0312839 A1 | 12/2009 | Scheker et al. |
| 2012/0136453 A1 | 5/2012 | Scheker et al. |
| 2017/0296350 A1 | 10/2017 | Orbay et al. |
| 2018/0140429 A1 | 5/2018 | Kakar et al. |

OTHER PUBLICATIONS

International Application No. PCT/US20/39183—Patent Cooperation Treaty PCT Written Opinion of the International Searching Authority—Completed Sep. 22, 2020 (dated Oct. 13, 2020).

DISTAL RADIOULNAR JOINT PROSTHESIS SYSTEM AND METHOD OF USE

CLAIM OF PRIORITY

This application is being filed as a non-provisional patent application under 35 U.S.C. § 111(a) and 37 CFR § 1.53(b). This application claims priority under 35 U.S.C. § 119(e) to U.S. provisional patent application Ser. No. 62/865,442 filed on Jun. 24, 2019, the contents of which are incorporated herein by reference.

FIELD OF INVENTION

The invention relates generally to prosthetic implants and in particular to prosthetic implants for the total or partial replacement of the distal radioulnar joint ("DRUJ").

BACKGROUND OF THE INVENTION

The DRUJ is a synovial pivot-type joint between the distal ends of the two bones in the forearm—the radius and the ulna. It is one of two joints between the radius and ulna, the other being the proximal radio ulnar Joint ("PRUJ"). The DRUJ is the articulation between the crescent-shaped convex distal head of ulna and the concave "sigmoid notch" on the distal radius.

The function of the DRUJ and PRUJ is to rotate the forearm and distribute loads from the wrist across the radius and ulna. The joints constrain the forearm to motion in one degree of freedom, pronation-supination. In simple words, this is a rotatory movement by which the forearm and hand rotate around the long axis of the forearm. In pronation, the palm of the hand faces downwards, while in supination, it faces upwards. In supination, the forearm can rotate from 0 degrees neutral to approximately 80-90 degrees. In pronation of the forearm can rotate from 0 degrees neutral to approximately 70-90 degrees.

In some cases of DRUJ dysfunction, replacement of the joint with a prosthesis is necessary to address bone pathology, degenerative changes, or trauma. Total DRUJ replacement prostheses can be constrained or unconstrained. In a constrained prosthesis, both radial and ulnar components are included, and the components are positively linked. In an unconstrained prosthesis, although ulnar and radial components may be included, they are not linked and function in much the same way as a healthy anatomic joint. Unconstrained prostheses often include a total replacement for the head of the ulna bone. Optionally, if the sigmoid notch in the radius (also sometimes referenced as the "ulnar notch" or "sigmoid cavity" of the radius) is damaged or otherwise dysfunctional, an unconstrained prostheses may include a component that is implanted on the radius to replace the sigmoid notch and provide an articulating surface for articulation with the replacement ulnar head.

The instant invention provides a novel unconstrained DRUJ prosthesis including a 3-piece replacement head system and, optionally, a cooperating sigmoid notch component. The three components of the replacement head system are a stem component adapted for implanting onto a prepared ulna, a head component adapted to pivotally engage the stem component, and a set screw to positively secure the head component to the stem component once the two components are in the desired pivotal alignment.

The replacement DRUJ prosthesis system can comprise several different sized stems components and head components providing options to a surgeon depending on the patient's anatomy and the desired interaction between the components.

It is an object of the present invention to provide a prosthesis for replacement of the distal radio ulnar joint to restore the pronation-supination motion of the forearm as well as stability between the ulna and radius.

It is another object of the present invention to provide a DRUJ prosthesis adapted for rotational alignment of the replacement joint along the axis of forearm rotation.

It is another object of the present invention to provide a DRUJ prosthesis which allows for the use of several different sized heads having differing geometries.

It is another object of the present invention to provide a DRUJ prosthesis adapted for variable pivoting alignment between the replacement distal ulnar head and the ulna.

It is another object of the present invention to provide a DRUJ prosthesis adapted for adjustment in the alignment between the articulating surface of the ulnar head and the sigmoid notch.

SUMMARY OF THE INVENTION

Disclosed is a DRUJ prosthesis system comprising an ulnar stem component, an ulnar head component, and a set screw.

The stem component comprises a substantially cylindrical elongated body having proximal and distal ends. The proximal end of the stem component comprises a medullary stem adapted for insertion into a prepared ulnar canal upon resection of the anatomical ulnar head. The distal end of the stem component comprises a spherical ball end attached to the stem component through a neck, the neck having a diameter substantially smaller than the diameter of the ball end. Interposed between the neck and the medullary stem is a flange which restraints the maximum penetration of the medullary stem into the ulnar canal.

The ulnar head component comprises an oblong body having a top surface, a bottom surface, an articulating surface, a rear surface, and two opposite side surfaces. The ulnar head component further comprises a ball cavity adapted to receive the stem component's ball end. The ball cavity is accessible through an entrance on either the rear or side surfaces having a diameter sufficiently wide to permit entry of the stem component's ball end. The ball cavity is also accessible through a bottom opening having a diameter sufficiently wide to accommodate the neck of the stem component, but narrower than the diameter of the stem component's ball end. The entrance and bottom opening are connected permitting insertion of the ball end of the stem component through the entrance and engagement of the stem component's neck with the bottom opening once the ball end is sufficiently inserted into the cavity.

The inner surface of the entrance of the ulnar head component is peripherally threaded. In some embodiments, the cavity is frusto-conical in shape, narrowing gradually between the entrance and the opposing wall of the cavity. In other embodiments, the cavity is cylindrical but lined with a plurality of splines that gradually increase in depth between the entrance and the opposing wall in the cavity. The frusto-conical cavity or splines are adapted for centering the stem component's ball end as it is inserted into the cavity. For maximum stability, the splines are sharp and adapted to partially penetrate the ball end of the stem component when sufficient pressure is applied to the ball end upon insertion into the cavity.

The articulating surface of the ulnar head component is cylindrically or spherically convex and, when projected onto a plane parallel to the top surface of the ulnar head, defines an arc having a center point. In some embodiments, the center point of the arc defined by the articulating surface is offset relative to a point projected from the longitudinal axis of the stem component which also traverses the center of the ball end of the stem component to the same parallel plane.

The set screw comprises a generally cylindrically shaped body having leading and trailing ends and a peripheral external thread between the two ends adapted to engage the thread on the inner surface of the entrance of the ulnar head component. The trailing end of the set screw includes a driving tool socket to permit the application of torque using a driving tool. The leading of the set screw optionally comprises a spike adapted to impinge on the ball end of the stem component when the set screw is torqued into the ulnar head/stem component assembly.

The DRUJ prosthesis system may optionally include a sigmoid notch component having an articulating surface and a bone-facing surface. The articulating surface is adapted to cooperate with the articulating surface of the ulnar head. The bone-facing surface is adapted to engage and be fastened to the sigmoid notch on the patient's radius. Engagement to the sigmoid notch is achieved by means of any method suitable, including, without limitation, screws, pegs, adhesives, and combinations thereof.

DETAILED DESCRIPTION OF THE INVENTION

The disclosed DRUJ prosthesis system comprises a stem component, an ulnar head, and a set screw. In instances where the anatomical sigmoid notch has deteriorated or is otherwise ineffective, an optional sigmoid notch component can be included.

Figure 1A:
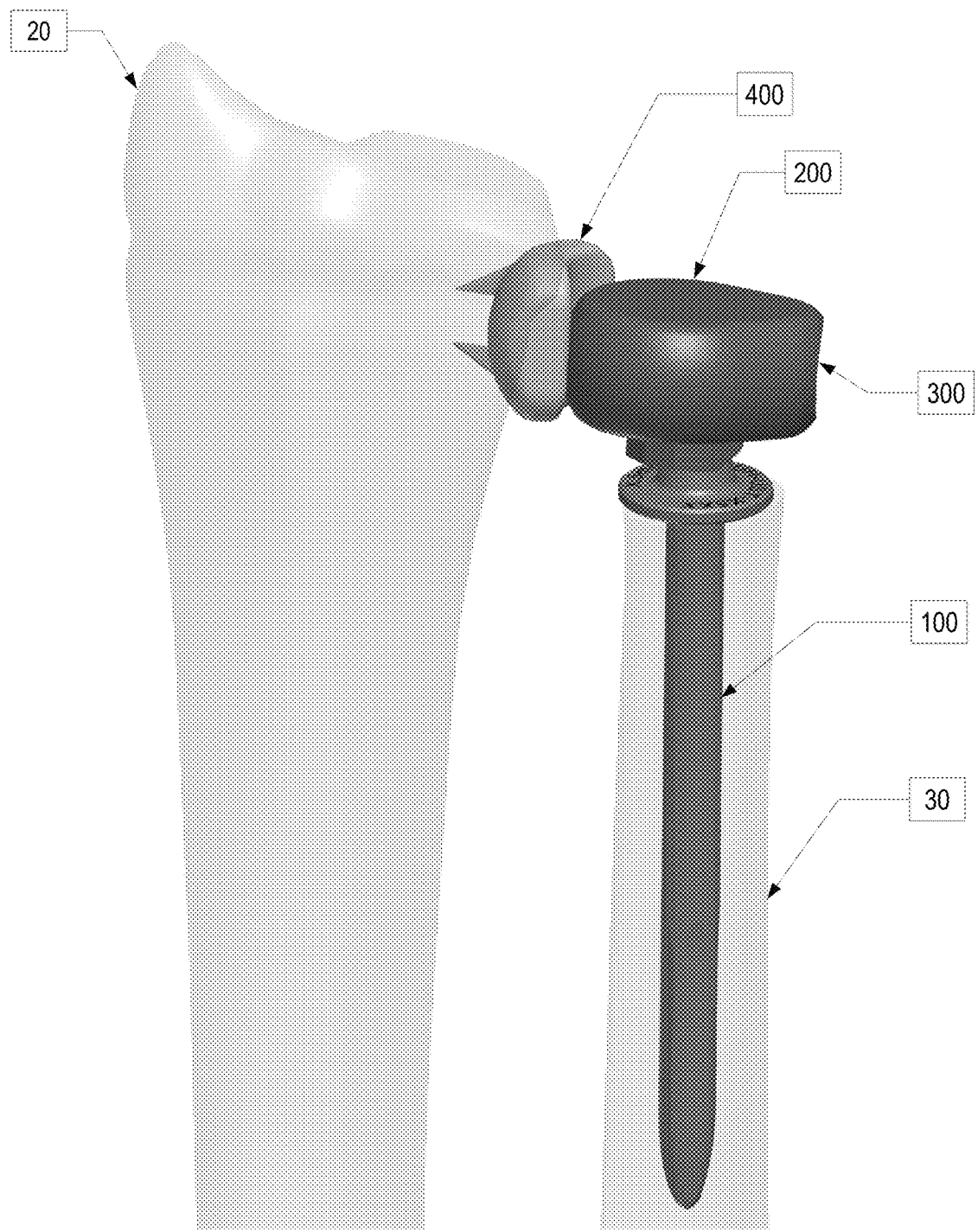
FIG. 1A is an assembled view of an embodiment of the present DRUJ prosthesis system adapted for replacement of the ulnar head and sigmoid notch, with the ulna and radius shown partially transparent to permit visualization of the various aspects of the components.
Figure 1B:
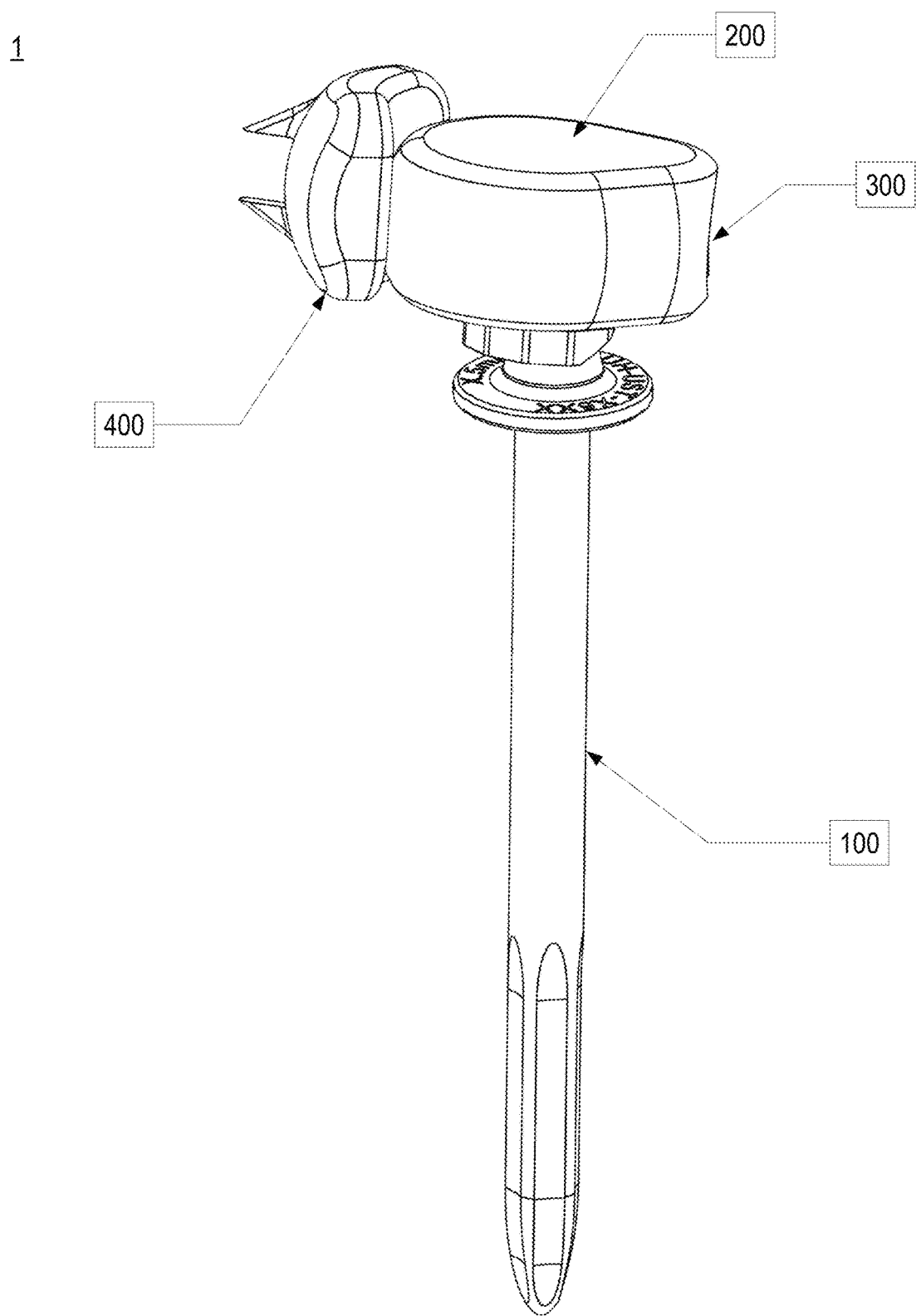
FIG. 1B is a different assembled view of the embodiment of FIG. 1A with the ulna and radius bones removed for clarity

Referring to FIGS. 1A and 1B shown is an embodiment of the present DRUJ prosthesis system adapted to completely replace the anatomical distal ulnar head and the sigmoid notch. FIG. 1A illustrates the system implanted with representations of the ulna and radius shown for reference. FIG. 1B shows the same embodiment with the bones completely removed for better visualization.

As is shown in FIGS. 1A and 1B the DRUJ prosthesis system 1 comprises a stem component 100, an ulnar head component 200, a set screw 300, and, optionally, a sigmoid notch component 400. The stem component 100 is implanted on the ulna 30 after resection of the damaged or dysfunctional anatomical distal ulnar head (not shown). The ulnar head component 200 is pivotally attached to the stem component 100 and secured into position by the set screw 300 once proper alignment is achieved. The optional sigmoid notch component 400 is attached to the radius 20 in alignment with the ulnar head component 200.

Figure 2:
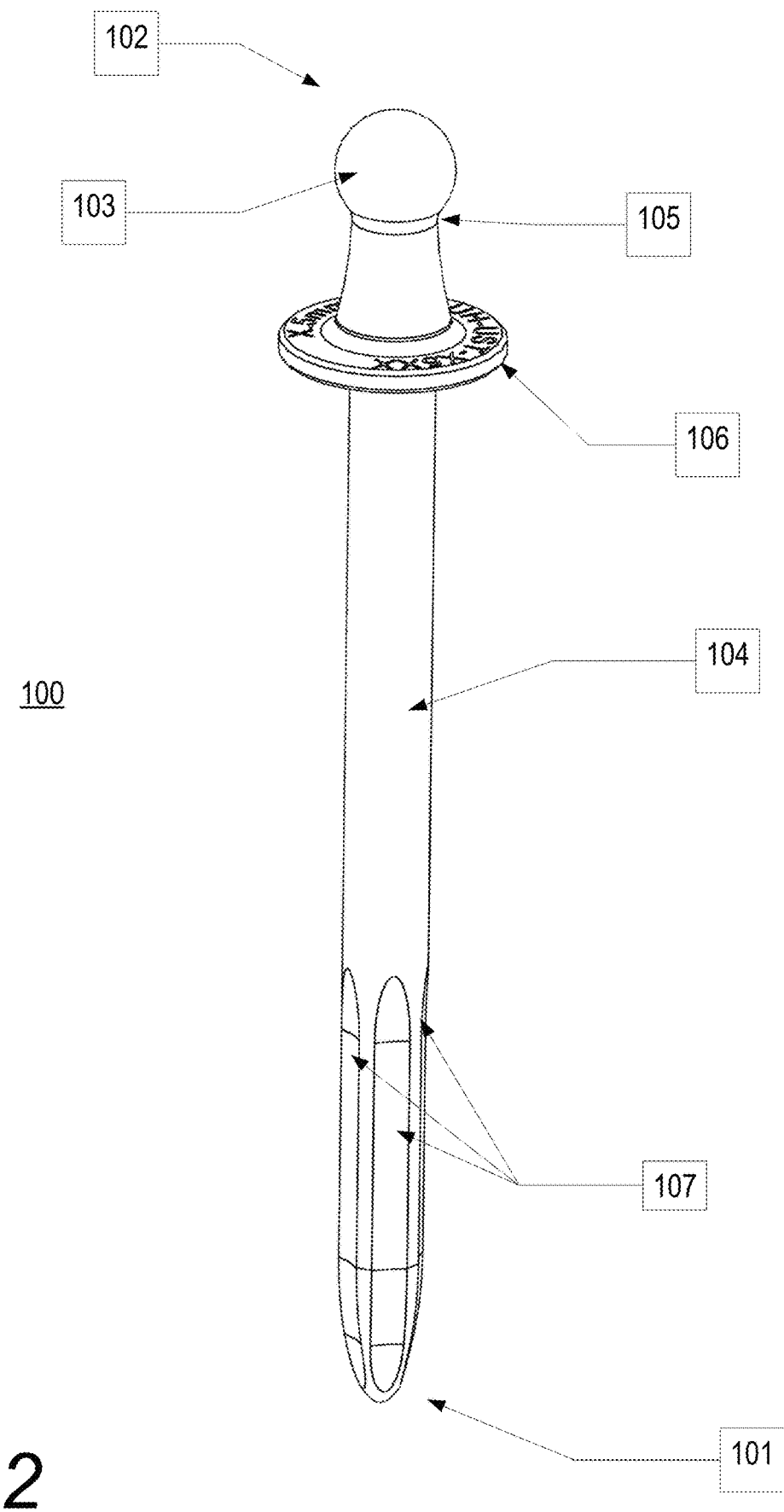
FIG. 2 is a stem component in accordance with an embodiment of the present invention.
Figure 3A:
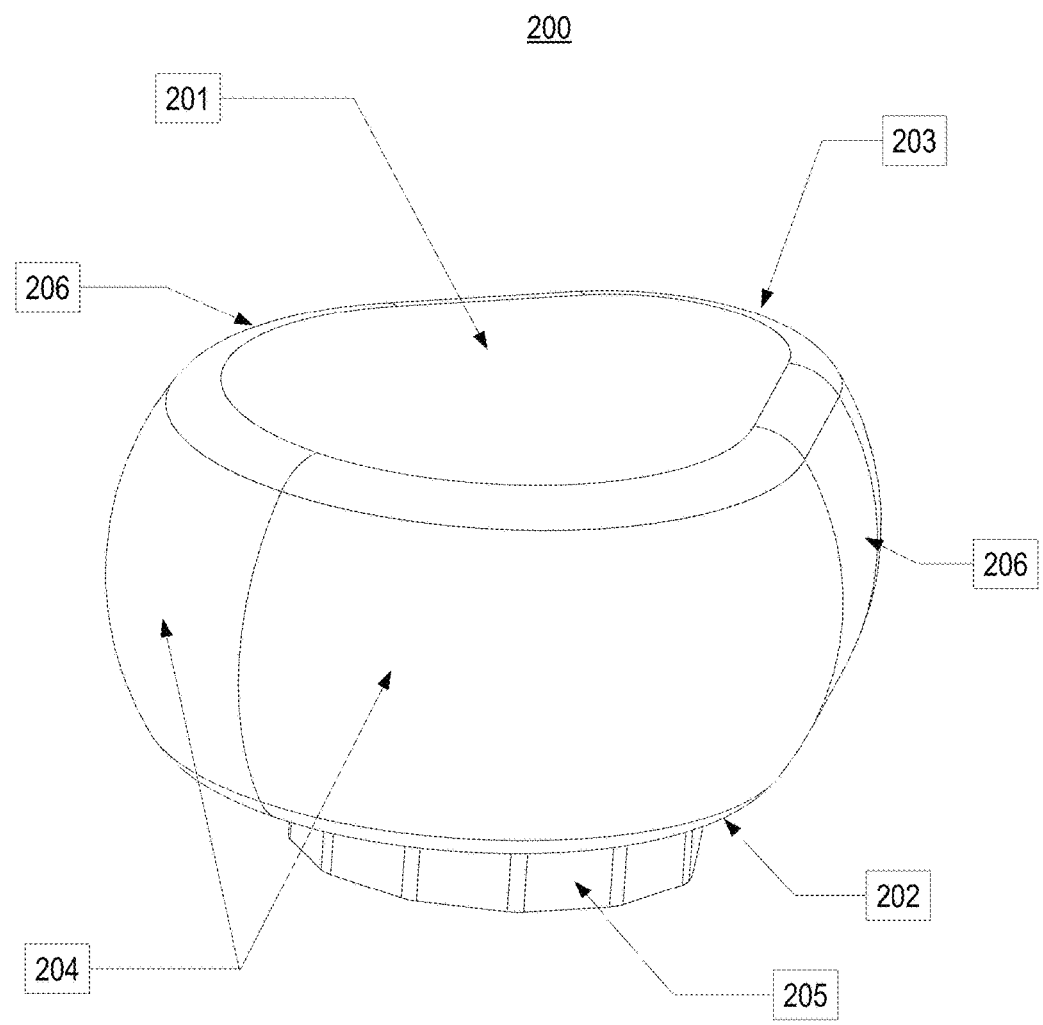
FIG. 3A is a front orthogonal view of an ulnar head component in accordance with an embodiment of the present invention.
Figure 3B:
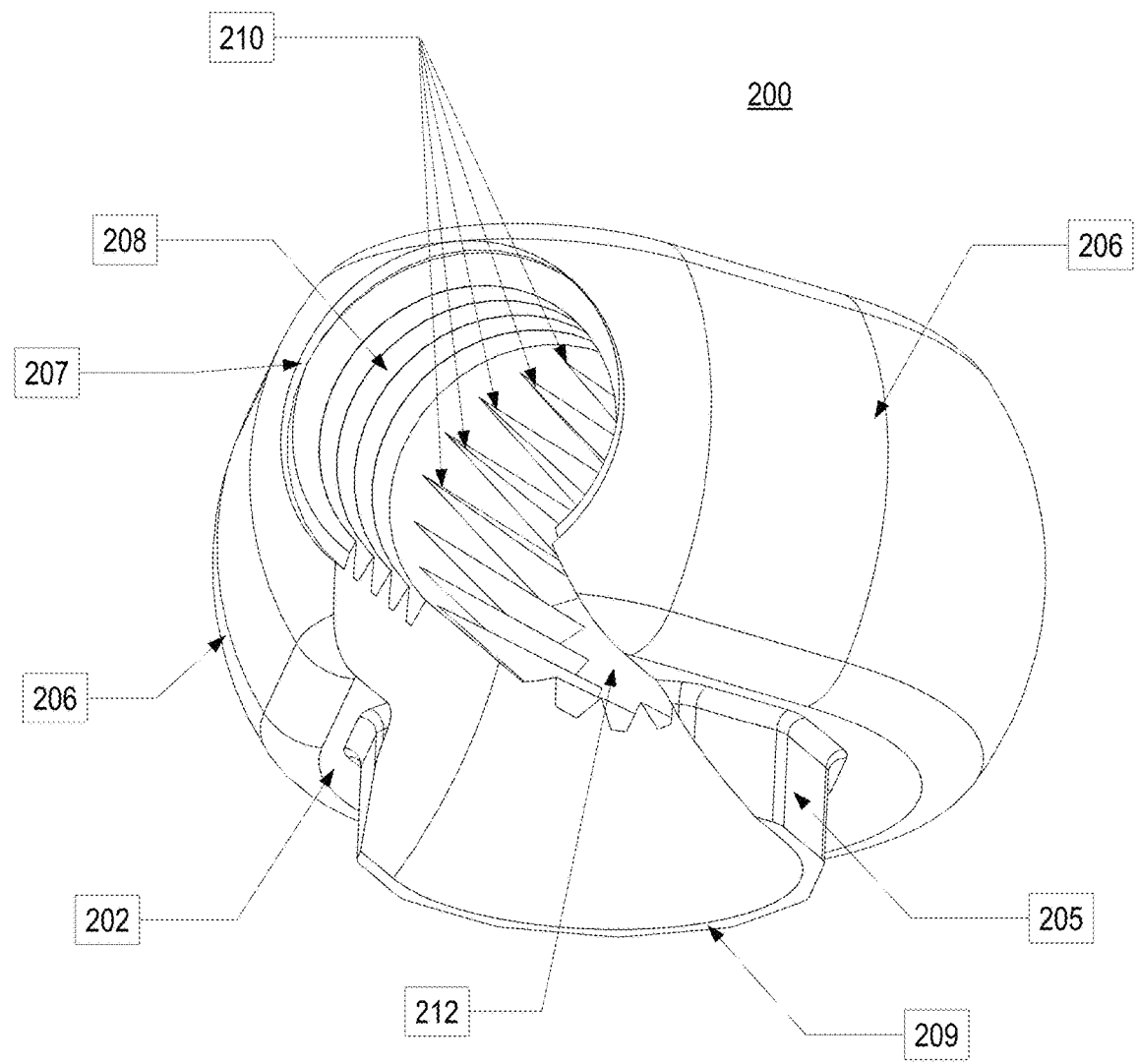
FIG. 3B is a rear orthogonal view of an ulnar head component in accordance with an embodiment of the present invention.
Figure 3C:
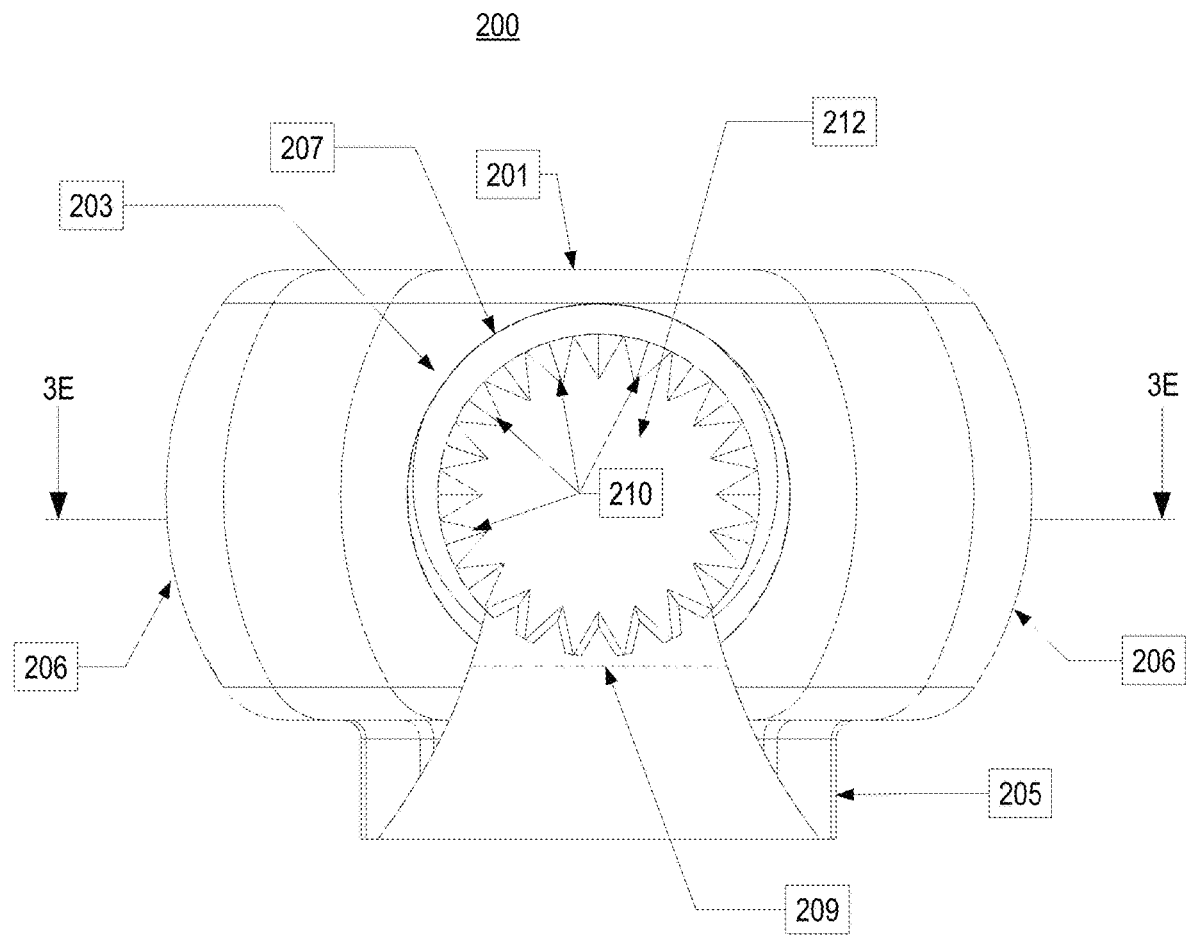
FIG. 3C is a rear view of an ulnar head component in accordance with an embodiment of the present invention.
Figure 3D:
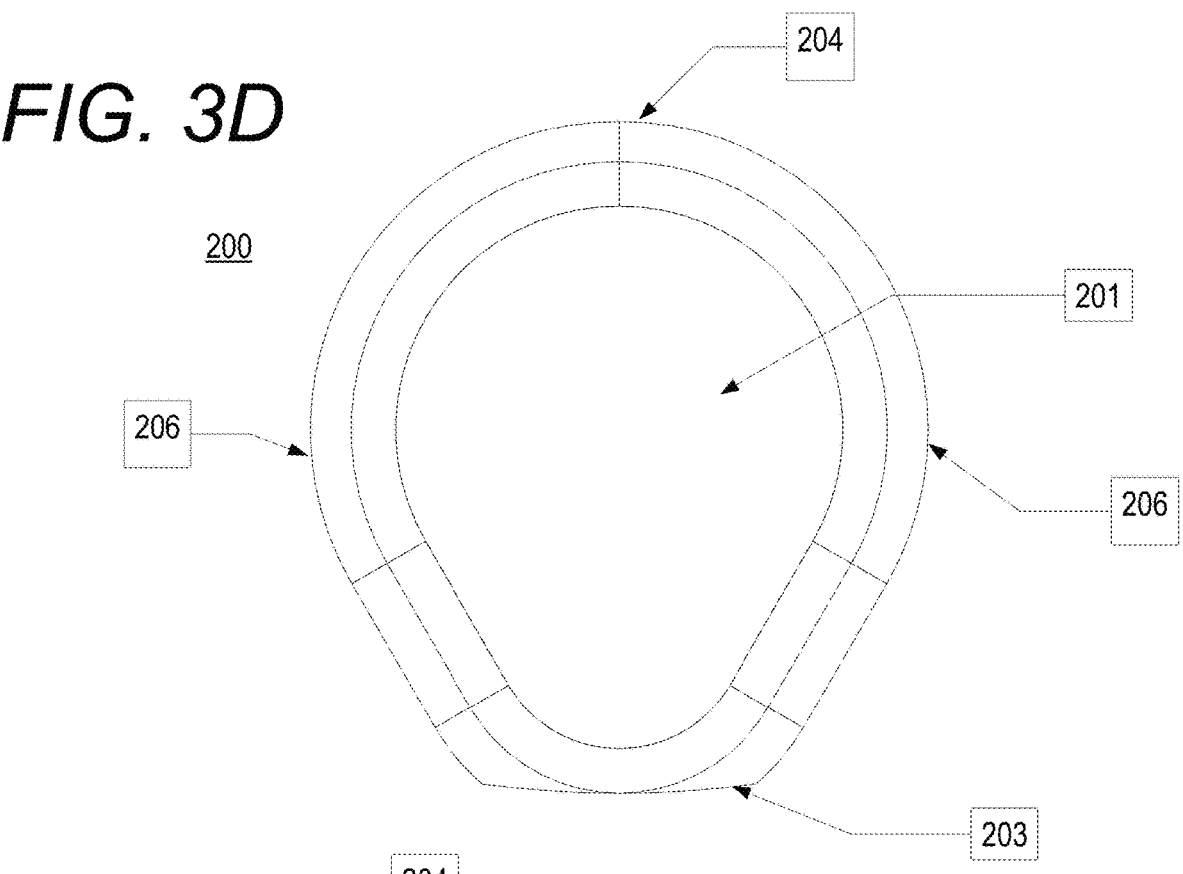
FIG. 3D is a top view of an ulnar head component in accordance with an embodiment of the present invention.
Figure 3E:
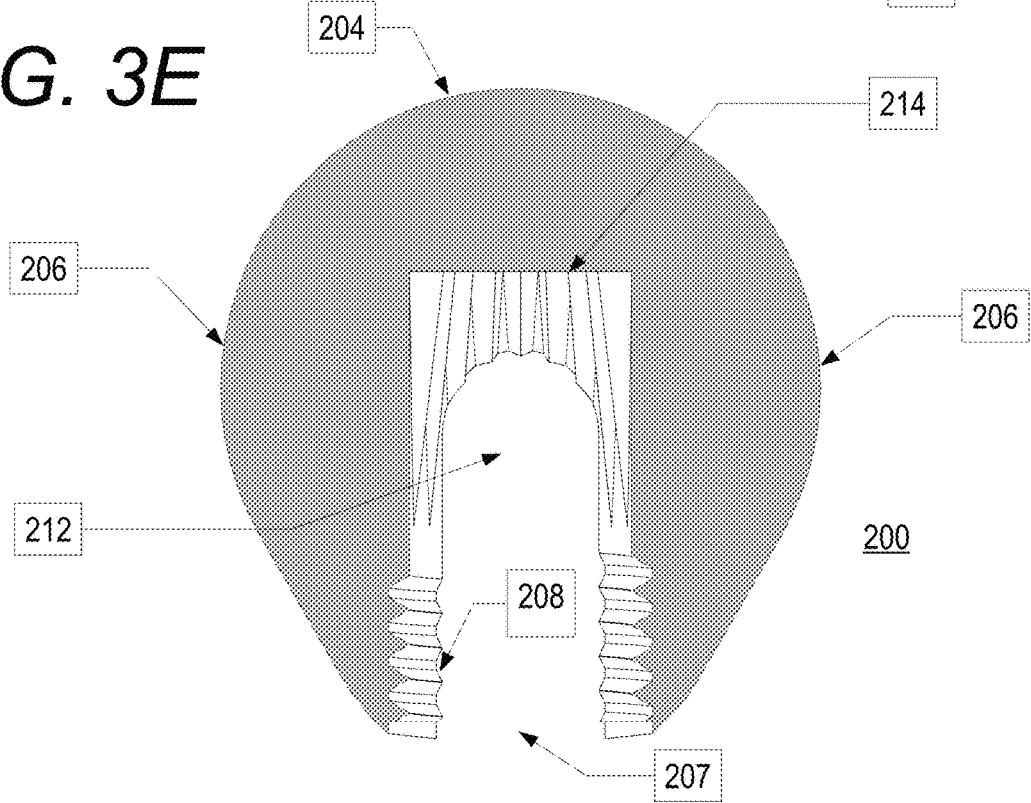
FIG. 3E is a cross sectional view of an ulnar head component in accordance with an embodiment of the present invention.

Shown in FIG. 2 is stem component 100 which comprises a substantially cylindrical elongated body 104 having a proximal end 101 and a distal end 102. The elongated body 104 comprises a medullary stem adapted for insertion into a prepared ulnar canal upon resection of the anatomical ulnar head. The proximal end 101 may optionally include one or more straight or spiral (not shown) flutes 107 to facilitate penetration of the prepared ulnar canal. Elongated body 104 and proximal end 101 may be smooth or may be partially or completely textured to promote faster bone growth. Proximal end 101 may be rounded, flat or pointed.

The distal end 102 of the stem component 100 comprises a spherical ball end 103 attached to the stem component through a neck 105. The neck 105 has a diameter that is substantially smaller than the maximum diameter of ball end 103. Disposed between the neck 105 and the medullary stem is a flange 106 which acts as a stop to exceed the maximum penetration depth of the medullary stem into the ulnar canal.

Shown in FIGS. 3A, 3B, 3C, 3D and 3E are various views of the ulnar head component 200 of the present invention.

The ulnar head component 200 comprises an oblong body having a top surface 201, a bottom surface 202, an articulating surface 204, a rear side 203, and two opposed side surfaces 206. The ulnar head component 200 further comprises a ball cavity 212 sized and adapted to receive the stem component's ball end 103. The ball cavity 212 is accessible through an entrance 207 on either the rear side 203 or either side surface 206 (the illustrated embodiment has a cavity entrance on rear side 203) having a diameter sufficiently wide to permit entry of the stem component's ball end 103.

The ball cavity is also accessible through a bottom opening 209 having a diameter sufficiently wide to accommodate neck 105 of the stem component 100, but narrower than the diameter of the ball end 103 of stem component 100. The entrance 207 and bottom opening 209 are connected permitting insertion of the ball end of the stem component 103 through the entrance 207 and engagement of the stem component's neck 105 with the bottom opening 209 once the ball end is sufficiently inserted into the cavity 212. It should be noted that due to the narrow diameter of the bottom opening 209, once the stem component 100 and ulnar head component 200 are assembled, the only way to disengage them is to slide ball end 103 back out through cavity entrance 207. The inner surface of the entrance 207 of the ulnar head component includes a peripheral internal thread 208.

The bottom opening 209 may optionally include a collar 205 to support stem neck 105 and to serve as an attachment point for an alignment tool (not shown) that can be used to properly align the ulnar head 200 and stem component 100.

In some embodiments (not shown), cavity 212 has smooth walls and is cylindrical in shape, having a diameter that closely matches that of ball end 103. In some embodiments (also not shown), cavity 212 has smooth walls and is frusto-conical in shape, narrowing gradually between the entrance 207 and the opposing wall 214 of the cavity 212. In other embodiments (shown here in FIGS. 3B and 3C but best observed in the cross sectional view shown in FIG. 3E), the cavity is cylindrical but lined with a plurality of splines 210 that gradually increase in depth between the entrance 207 and the opposing wall 214 of the cavity 212. The frusto-conical cavity (not shown) or splines 210 are adapted to center the stem component's ball end 103 as it is inserted into the cavity 212. For maximum stability, the splines 210 may have sharp edges and be adapted to penetrate the ball end 103 of the stem component 100 when sufficient pressure is applied to the ball end 103 upon insertion into the cavity 212.

Figure 4:
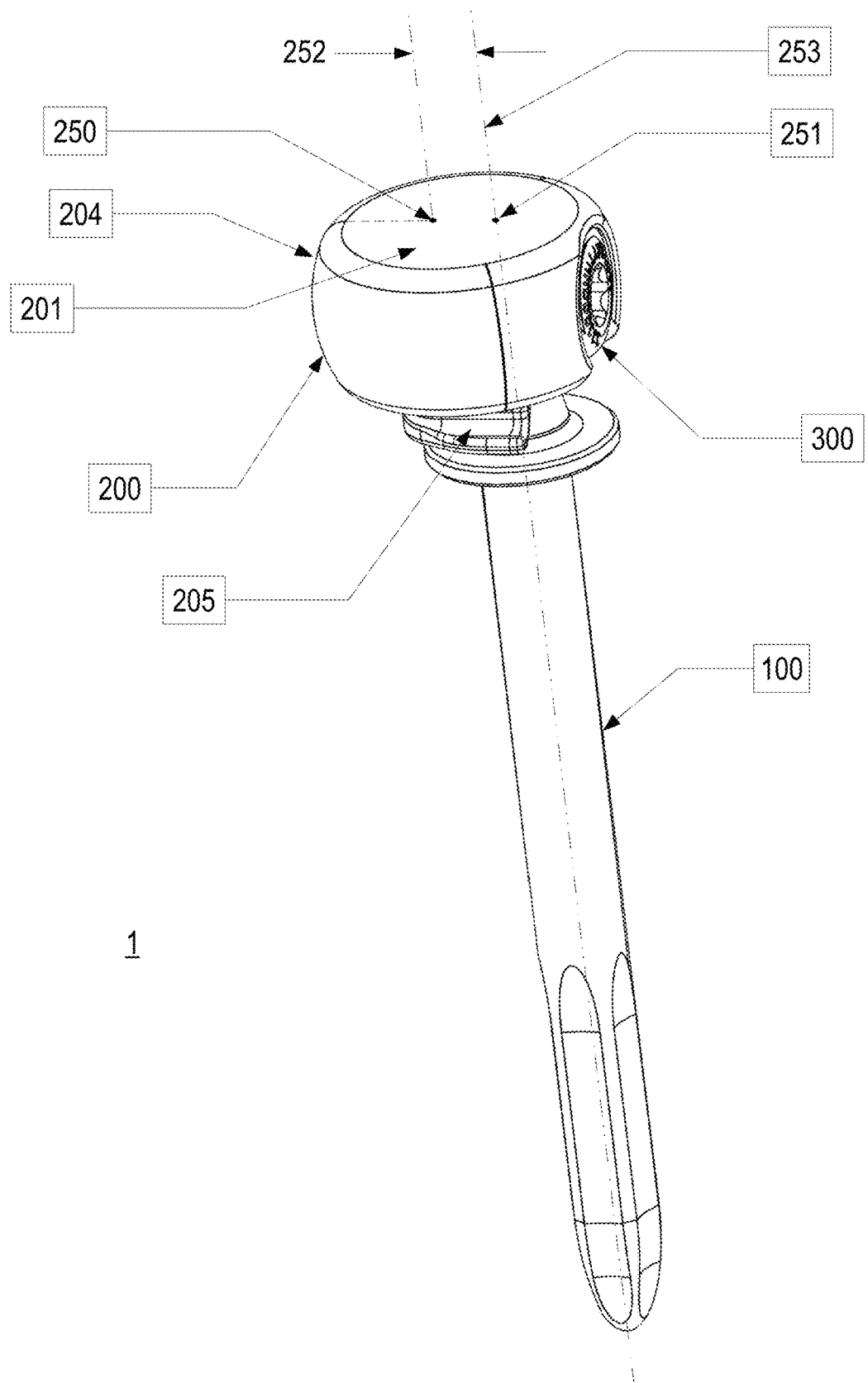
FIG. 4 is an assembled view of an ulnar head component and a stem component in accordance with the present invention illustrating the ulnar head articulating surface offset relative to the stem component's longitudinal axis.

As shown in FIG. 4, the articulating surface 204 of the ulnar head component 200 is cylindrically or spherically convex and, when projected onto an imaginary plane parallel to the top surface 201 of the ulnar head, defines an arc having a center point 250. In some embodiments, the center point 250 of the arc defined by the articulating surface 204 is offset relative to a point projected onto the same imaginary plane by the longitudinal axis 253 of stem component 100 which also traverses the center of the ball end 103 of the stem component 100. The length of this offset 252 can vary depending on the geometry of the ulnar head 200 selected. Offset 252 can range from zero, to the range normally found in the anatomy of a healthy ulnar head (1.1 mm-3.9 mm), or greater. A greater-than-anatomical offset could be used in situations where a greater tensioning force of the ligaments between the radius and ulna is desirable.

Figure 5A:
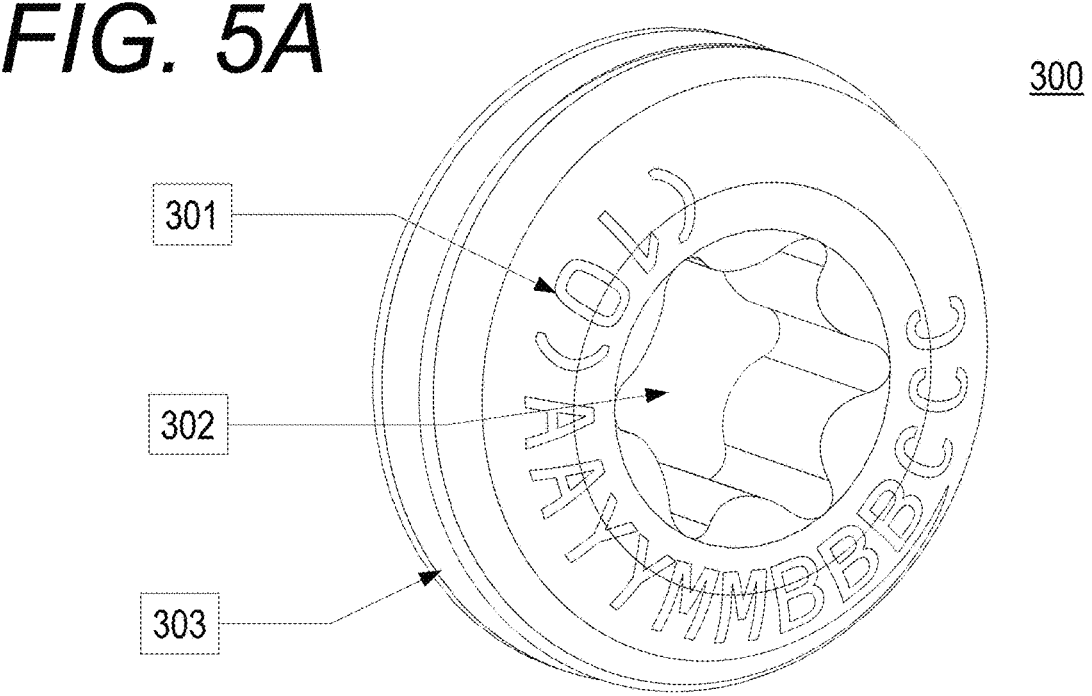
FIG. 5A is a rear orthogonal view of a set screw in accordance with an embodiment of the present invention.
Figure 5B:
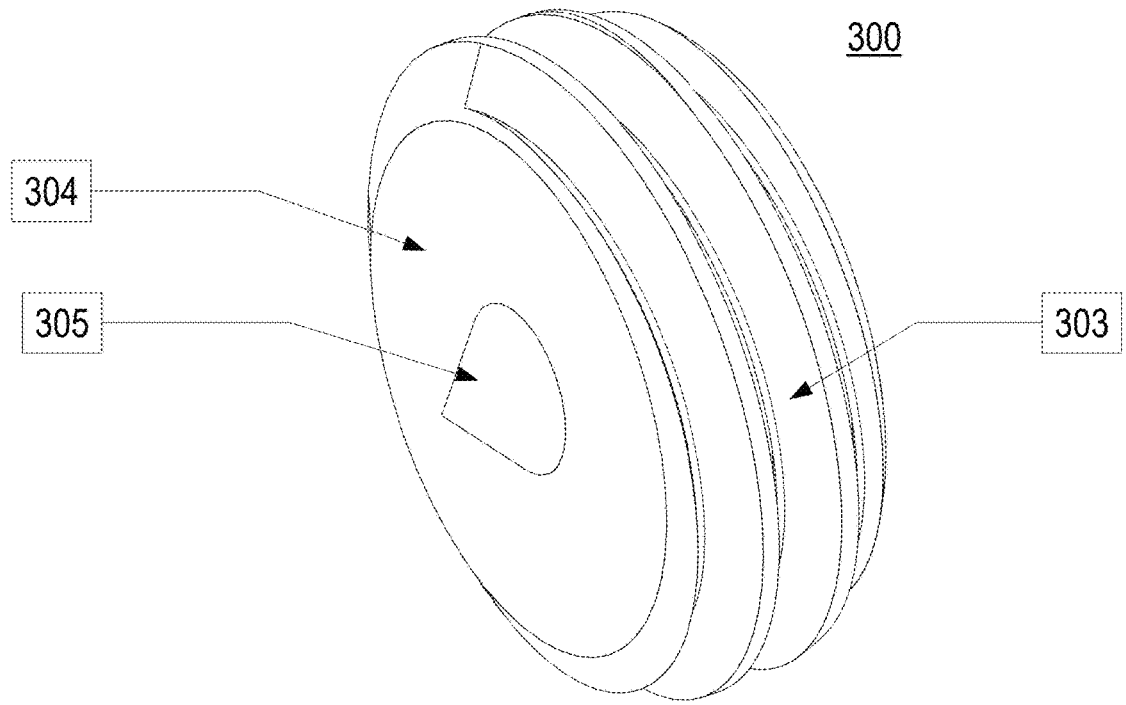
FIG. 5B is a front orthogonal view of a set screw in accordance with an embodiment of the present invention.

Referring next to FIGS. 5A and 5B, set screw 300 comprises a generally cylindrically shaped body having a leading end 304 and a trailing end 301 and a peripheral external thread 303 between the two ends. Thread 303 is adapted to engage the thread 208 on the inner surface of the entrance 207 of the ulnar head component 200. The trailing end 301 of set screw 300 includes a driving tool socket 302 to permit the application of torque using a matching driving tool (not shown). The leading end 304 of set screw 300 optionally comprises a spike 305 adapted to impinge on, and partially penetrate, the ball end 103 of the stem component 100 when set screw 300 is torqued into the entrance 207 and thread 208 of the ulnar head 200 once assembled with the stem component 100.

The stem component 100, ulnar head component 200, and set screw 300 are preferably each of unitary construction. The material used for each of the components is any suitable bio-compatible metallic material having the required strength and durability to withstand the loads normally imposed on the DRUJ. As discussed above, in order to achieve maximum stability once the various components are implanted and properly aligned, the spike 305 of the set screw 300, as well as the splines 210 of the ulnar head 200 are designed to impinge on, and partially penetrate the ball end 103 of the stem component 100. To achieve this result, it is desirable to use a material for the stem component 100 that is slightly softer than that used in the ulnar head component 200 and the set screw 300. An exemplary suitable combination of materials is cobalt-chromium for the ulnar head 200 and set screw 300 and titanium for the stem component 100.

Figure 6A:
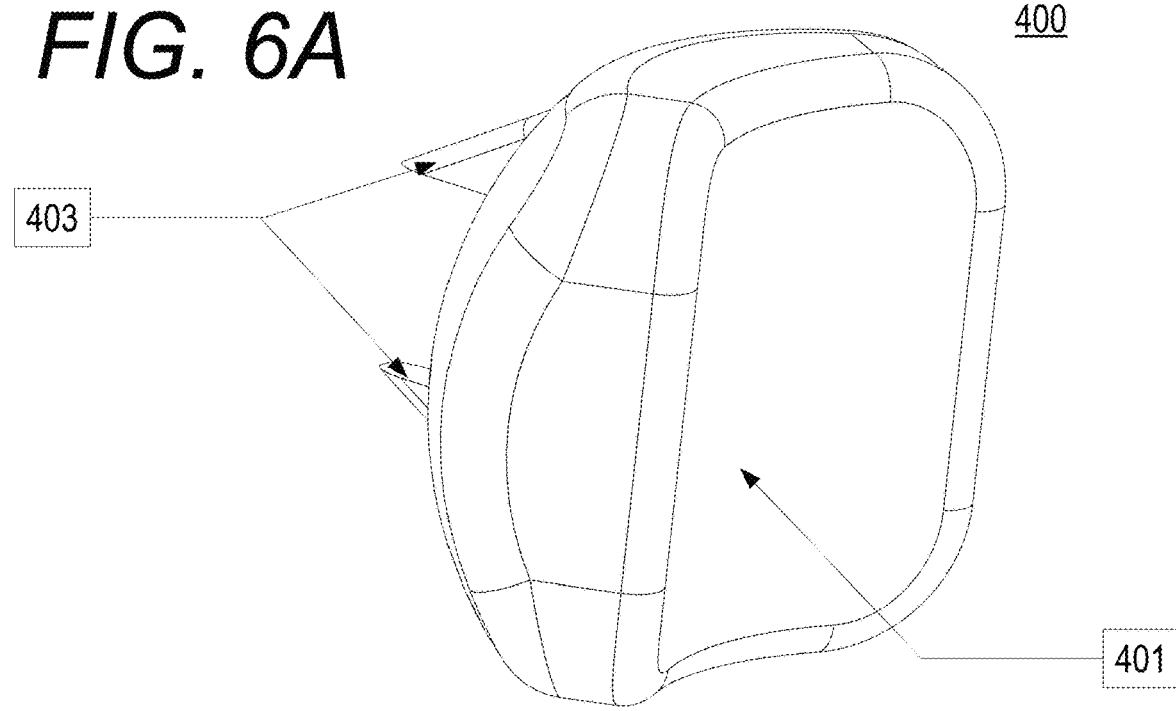
FIG. 6A is a front orthogonal view of a sigmoid notch component in accordance with an embodiment of the present invention illustrating the offset feature.
Figure 6B:
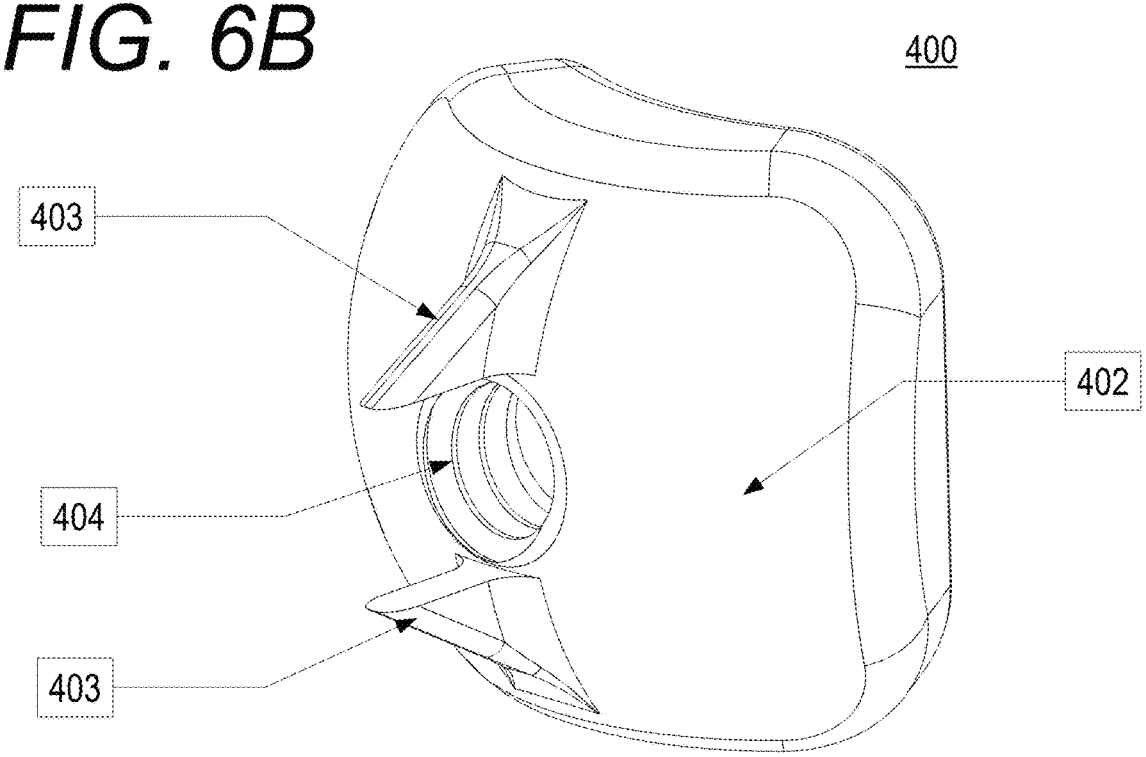
FIG. 6B is a rear orthogonal view of a sigmoid notch component in accordance with an embodiment of the present invention illustrating the offset feature.

The DRUJ prosthesis system 1 may optionally include a sigmoid notch component 400 such as that illustrated in FIGS. 6A and 6B. Sigmoid notch component 400 comprises articulating surface 401 and a bone-facing surface 402. The articulating surface 401 is adapted to cooperate with the articulating surface 204 of the ulnar head 200. The bone-facing surface 402 is adapted to engage and be fastened to the sigmoid notch on the patient's radius. Engagement to the sigmoid notch is achieved by means of any method suitable, including, without limitation, screws, pegs, adhesives, stems, 3D-printed meshes, and combinations thereof. To this end, the bone-facing surface may include one or more pegs or spikes 403 and one or more threaded holes 404 to accept a bone screw. Suitable materials for sigmoid notch component 400 include, without limitation, ultra-high-molecular-weight polyethylene (UHMWPE) including highly cross-linked varieties, polyetheretherketone (PEEK), and polyphenylsulfone (PPSU). In addition, bone-facing surface 402 may be manufactured from titanium or other osteointegrating metal.

Method of Use

In operation, the surgeon first gains clear access to the site of the ulnar head to be replaced and resects the ulnar head by performing a cut across the ulna below the ulnar head. Once resected, the ulnar head is measured to determine the appropriate size of ulnar head component 200 to be used as a prosthesis. Next, the ulnar canal is identified on the ulna and the opening to the ulnar canal is marked using an awl or similar tool. The ulnar canal is next reamed and expanded to a diameter and depth suitable for insertion of the medullary stem of stem component 100. The cut surface of the ulna can then be prepared with a planer to ensure it is substantially flat and perpendicular to the prepared medullary canal.

The stem component 100 is next inserted into the prepared medullary canal until set, with flange 106 in flush contact with the cut surface of the ulna. With the stem component 100 in place, the ulnar head component 200 is next mated to it by introducing the ball end 103 of stem component 100 through entrance 207 of the ulnar head component 200. The ball end 103 is inserted until neck 105 is seated in bottom opening 209. Set screw 300 is next threaded into entrance 207 to prevent ball end 103 from exiting the ulnar head 200 but set screw 300 is not completely fastened. At this point, with set screw 300 not fastened, ulnar head 200 is free to pivot and swivel with respect to stem component 100.

Next, an alignment tool (not shown) may be placed on collar 205 of the ulnar head 200 and manipulated as necessary to align ulnar head 200 with other anatomical features of the patient. For example, an alignment tool may be used to align the axis of rotation of the replacement ulnar head with the axis of rotation of the forearm. Once the proper alignment is reached, set screw 300 is fully torqued causing spike 305 and splines 210 to impinge and partially penetrate ball end 103.

If it is determined that the anatomical sigmoid notch is damaged or ineffective, the sigmoid notch component 400 may be implanted by aligning the articulating surface 401 of the sigmoid notch component 400 with the articulating surface 204 of the ulnar head component 200 and affixing the sigmoid notch component 400 to the radius bone.

Although the present invention is described above in connection with certain embodiments and options, these descriptions are not intended to be limiting as various modifications may be made therein without departing from the spirit of the invention and within the scope and range of equivalent of the described embodiments.

We claim:

1. A distal radioulnar joint prosthesis system comprising:
   an ulnar stem component comprising an elongated cylindrical body having a proximal end and a distal end, the proximal end adapted for insertion into a ulnar medullary canal, the distal end comprising a spherical ball end attached to the ulnar stem body by means of a neck having a diameter narrower than the spherical ball end, and a flange disposed between the neck and the ulnar stem body;
   an ulnar head component comprising an oblong body having a top surface, a bottom surface, an articulating surface, a rear surface, two opposite side surfaces, an interior cavity adapted to receive the ulnar stem component's ball end, an entrance to the cavity having a diameter sufficient to accommodate the ulnar stem component's ball end, internal threads disposed on the entrance, and a bottom opening to the cavity having a diameter sufficiently wide to accommodate the neck of the ulna stem component but being narrower than the diameter of the ball end of the ulna stem component, wherein the entrance to the cavity is connected to the bottom opening; and
   a substantially cylindrical set screw having a trailing end including a driving tool socket, a leading end with a spike adapted to partially penetrate, and fix a position, of the ball end of the ulnar stem component, and a peripheral thread adapted to engage the internal threads disposed on the entrance of the ulnar head component.

2. The distal radioulnar joint prosthesis system of claim 1, further comprising a sigmoid notch component having a bone-contacting side adapted to engage and affix to the sigmoid notch of the radius bone, and an opposed articulating surface adapted to cooperate with the articular surface of the ulnar head component.

3. The distal radioulnar joint prosthesis system of claim 1, wherein the cavity of the ulnar head component is smooth and frusto-conical in shape with a diameter narrowing gradually from the entrance of the ulnar head component.

4. The distal radioulnar joint prosthesis system of claim 1, wherein the cavity of the ulnar head component is cylindrical and further includes a plurality of splines having a depth that gradually increases from the entrance of the ulnar head component, the plurality of splines adapted to partially penetrate, and fix the position, of the ball end of the ulna stem component.

5. The distal radioulnar joint prosthesis system of claim 1, wherein the entrance of the cavity of the ulnar head component is located on the rear surface of the ulnar head component.

6. The distal radioulnar joint prosthesis system of claim 1, wherein the entrance of the cavity of the ulnar head component is located on one of the side surfaces of the ulnar head component.

7. A method for replacing a distal radioulnar joint of a patient comprising the steps of:
   removing a head of an ulna in the radioulnar joint;
   expanding an ulnar medullary canal on the ulna;
   flattening a cut surface of the ulna;
   inserting a stem component into the expanded ulnar medullary canal, the stem component comprising an elongated cylindrical body having a proximal end and a distal end, the proximal end adapted for insertion into the ulnar medullary canal, the distal end comprising a spherical ball end attached to the ulnar stem body by means of a neck having a diameter narrower than the spherical ball end, and a flange disposed between the neck and the ulnar stem body;
   continuing to insert the stem component into the expanded ulnar medullary canal until the flange contacts the cut surface of the ulna;
   attaching an ulnar head component to the distal end of the stem component, the ulnar head component comprising an oblong body having a top surface, a bottom surface, an articulating surface, a rear surface, two opposite side surfaces, an interior cavity adapted to receive the ulnar stem component's ball end, an entrance to the cavity having a diameter sufficient to accommodate the ulnar stem component's ball end, internal threads disposed on the entrance, and a bottom opening to the cavity having a diameter sufficiently wide to accommodate the neck of the ulna stem component but being narrower than the diameter of the ball end of the ulna stem component;
   securing the ulnar head component to the stem component using a set screw, the set screw comprising a substantially cylindrical set screw having a trailing end including a driving tool socket, a leading end with a spike adapted to partially penetrate, and fix a position, of the ball end of the ulnar stem component, and a peripheral thread adapted to engage the internal threads disposed on the entrance of the ulnar head component; and
   attaching a sigmoid notch component to a sigmoid notch of a radius, the sigmoid notch component comprising a bone-contacting side adapted to engage and affix to the sigmoid notch of the radius, and an opposed articulating surface adapted to cooperate with the articular surface of the ulnar head component.

\* \* \* \* \*